United States Patent [19]
Chancellor

[11] Patent Number: 5,752,978
[45] Date of Patent: May 19, 1998

[54] DETRUSOR MYOPLASTY AND NEURO-MUSCULAR ELECTRICAL STIMULATION

[75] Inventor: Michael B. Chancellor, Moorestown, N.J.

[73] Assignee: Thomas Jefferson University, Philadelphia, Pa.

[21] Appl. No.: 663,153

[22] PCT Filed: Dec. 6, 1994

[86] PCT No.: PCT/US94/13959

§ 371 Date: Jun. 13, 1996

§ 102(e) Date: Jun. 13, 1996

[87] PCT Pub. No.: WO95/16491

PCT Pub. Date: Jun. 22, 1995

Related U.S. Application Data

[63] Continuation-in-part of Ser. No. 166,211, Dec. 13, 1993, Pat. No. 5,370,670.

[51] Int. Cl.$^6$ .......................................... A61N 1/08
[52] U.S. Cl. ................................................ 607/40
[58] Field of Search .............................. 607/40, 41

[56] References Cited

U.S. PATENT DOCUMENTS

| | | |
|---|---|---|
| 4,205,671 | 6/1980 | Lassen . |
| 5,188,104 | 2/1993 | Wernicke et al. ............ 607/40 |
| 5,199,430 | 4/1993 | Fang et al. . |
| 5,231,997 | 8/1993 | Kikuchi et al. ............ 607/154 |
| 5,370,670 | 12/1994 | Chancellor ................. 607/40 |

OTHER PUBLICATIONS

Acker, M. et al., "Skeletal Muscle as the Potential Power Source for a Cardiovascular Pump: Assessment in Vivo", *Science* 1987, 236, 324–327.

Alexander, S. And Rowan, "Electrical Control of Urinary Incontinence by Radio Implant", *Brit. J. Surg.* 1968, 55, 358–364.

Boyce, W. et al., "Research Related to the Development of an Artificial Electrical Stimularo for the Paralyzed Human Bladder: A Review", *The J. of Urology* 1964, 91(1), 41–51.

Brindley, G.S. et al., "Sacral Anterior Rott Simulators for Bladder Control in Paraplegia: the First 50 Cases", *J. of Neurology, Neurosurgery and Psychiatry* 1986, 49, 1104–1114.

Buyukunal, S.N.C. et al., "An Alternative Treatment Modality in Closing Bladder Exstrophy: Use of Rectus Abdominus Muscle Flap—Preliminary Results in a Rat Model", *J. Of Pediatric Surg.* 1989, 24(6), 586–589.

Carpentier et al., "Myocardial Substitution with a Stimulated Skeletal Muscle: First Successful Clinical Case", *Lancet* 1985, 1, 1267.

Chachques et al., "Effect of Latissimus Dorsi Dynamic Cardiomyoplasty on Ventricular Function", *Circulation* 1988, 78, 203–216.

Magovern, G. et al., "Paced Skeletal Muscle for Dynamic Cardiomyoplasty", *Ann. Thorac. Surg.* 1988, 45, 614–619.

Merrill, D.C. et al., "Clinical Experience with the Mentor Bladder Stimulator. II. Meningomyelocele Patients", *J. Urol.* 1974, 112, 823–825.

(List continued on next page.)

*Primary Examiner*—Scott M. Getzow
*Attorney, Agent, or Firm*—Woodcock Washburn Kurtz Mackiewicz & Norris, LLP

[57] ABSTRACT

An implantable micturition inducer is disclosed. The device comprises an implantable actuatable signal generator that comprises one or more switches and a power source, and at least one electrical lead having one end connected to the signal generator and the other end adapted to be connected to muscle transected to form a muscle bag around an individual's bladder. Actuation of the switch or switches results in the delivery of a series of stimulus pulses from the signal generator to the muscle bag which are sufficient to cause the muscle bag to contract and thereby induce micturation on demand. Methods for inducing micturition in patients with areflexic bladders or an otherwise diminished capacity to intentionally micturate are disclosed.

16 Claims, 10 Drawing Sheets

OTHER PUBLICATIONS

Merrill et al., "Clinical Experience with the Mentor Bladder Stimulator. I. Patients with Upper Motor Neuron Lesions", *J. Urol.* 1974, 112, 52–56.

Peckham, P.H. et al., "Alteration in the Force and Fatigability of Skeletal Muscle in Quadriplegic Human Following Exercise Induced by Chronic Electrical Stimulation", *Clin. Orthop.* 1976, 114, 326–334.

Rivlin, A.S. et al., "Objective Clinical Assessment of Motor Funciton after Experimental Spinal Cord Injury in the Rat", *J. Neurosurg.* 1977, 47, 577–581.

Salmons, S. et al., "The Influence of Activity of Some Contractile Characteristics of Mammalian Fast and Slow Muscles", *J. Physiol.* 1969, 201, 535–549.

Tanagho, E.A. et al., "Neural Stimulation for Control of Voiding Dysfunctions: A Preliminary Report in 22 Patients with Serious Neuropathic Voiding Disorders", *J. Urol.* 1989, 142, 340–345.

Tarlov, I.M., "Spinal Cord Compression Studies", *Arch. Neurol. Psychiatry* 1954, 71, 588–597.

Timm, G.W. and Bradley, "Electrostimulation of the Urinary Detrusor to Effect Contraction and Evacuation", *Invest. Urol.* 1969, 6, 562–568.

Yu–Hai, Z. et al., "Enveloping the Bladder with Displacement of Flap of the Rectus Abdominis Muscle for the Treatment of Neurogenic Bladder", *J. Urol.* 1990, 144, 1194–1195.

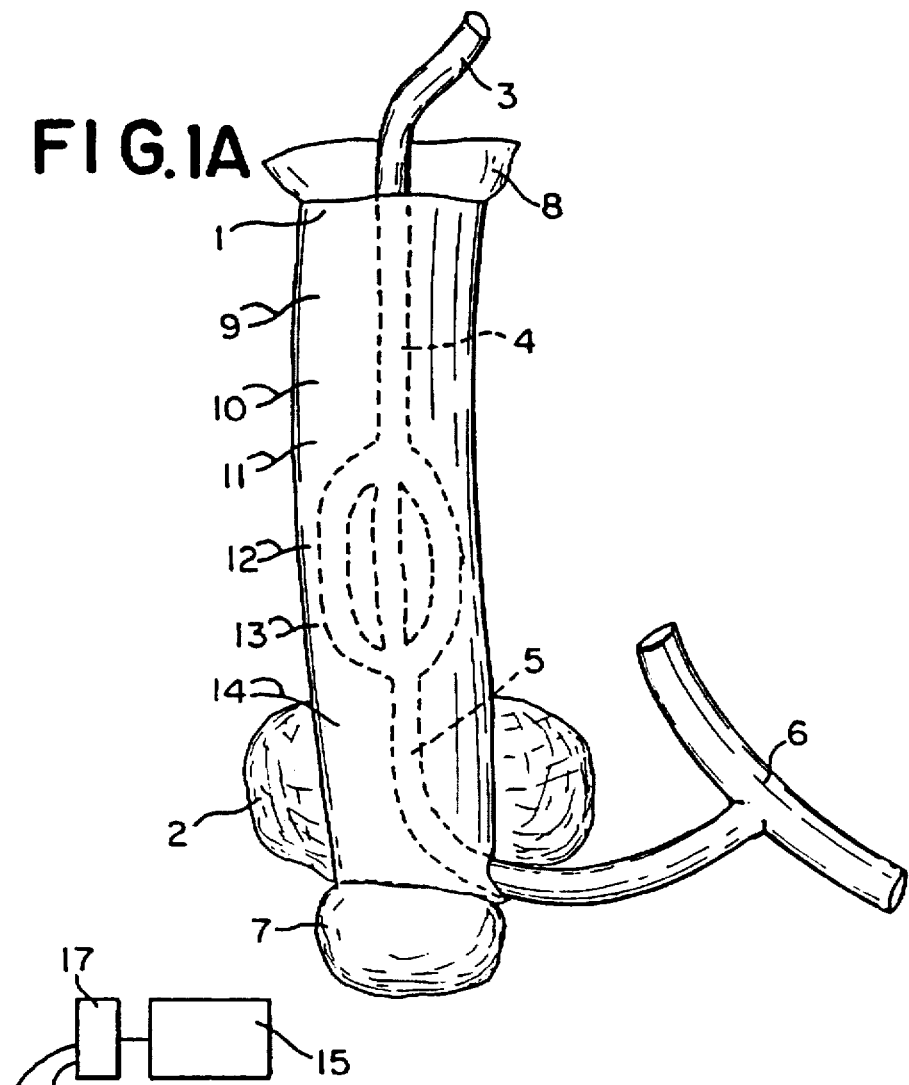
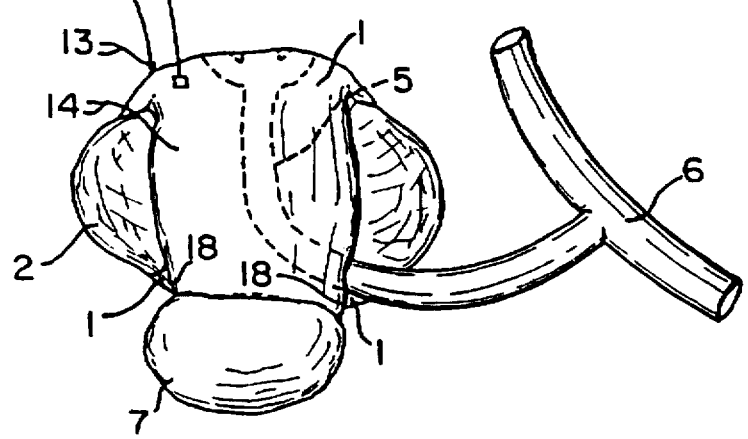

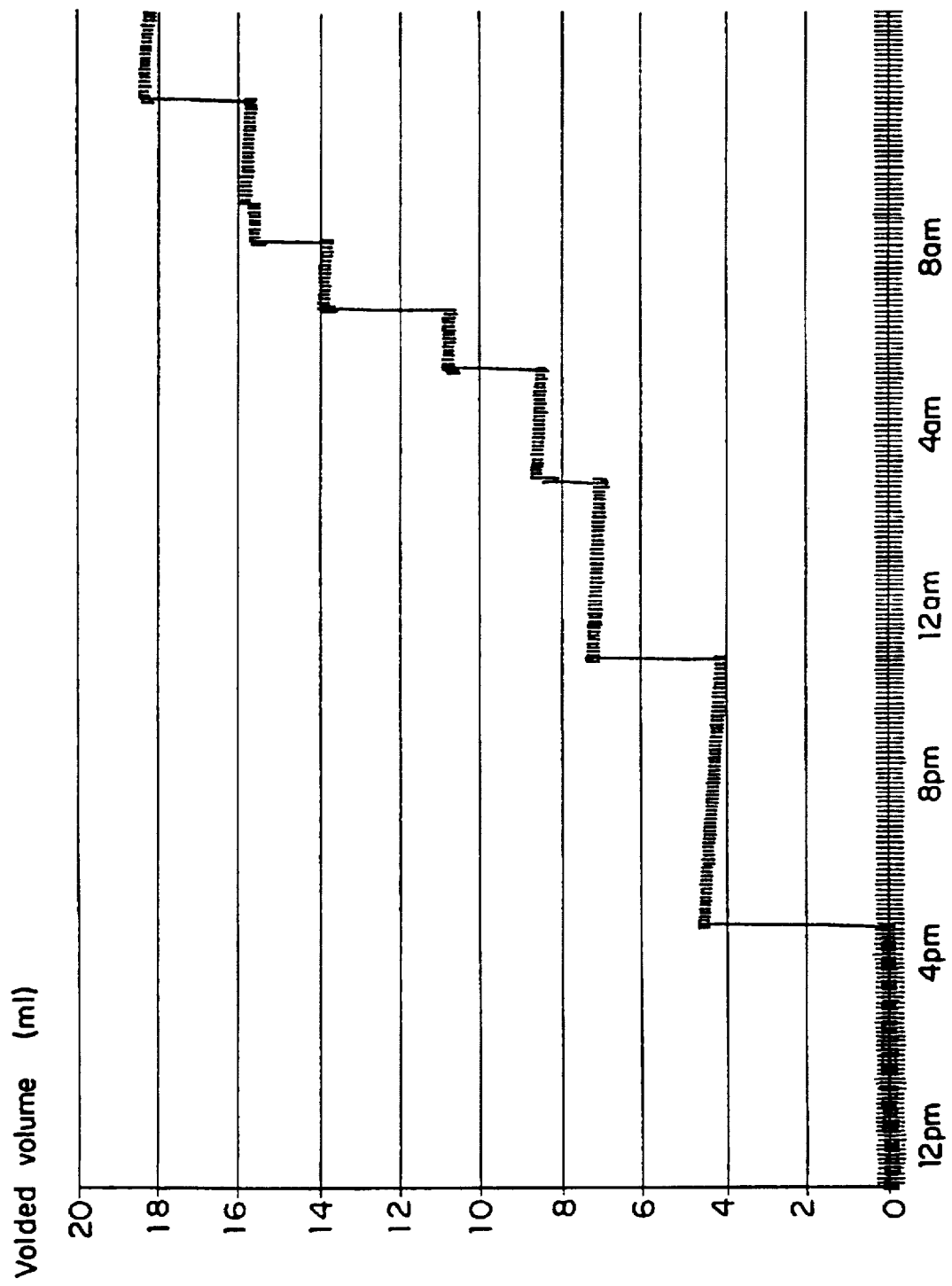

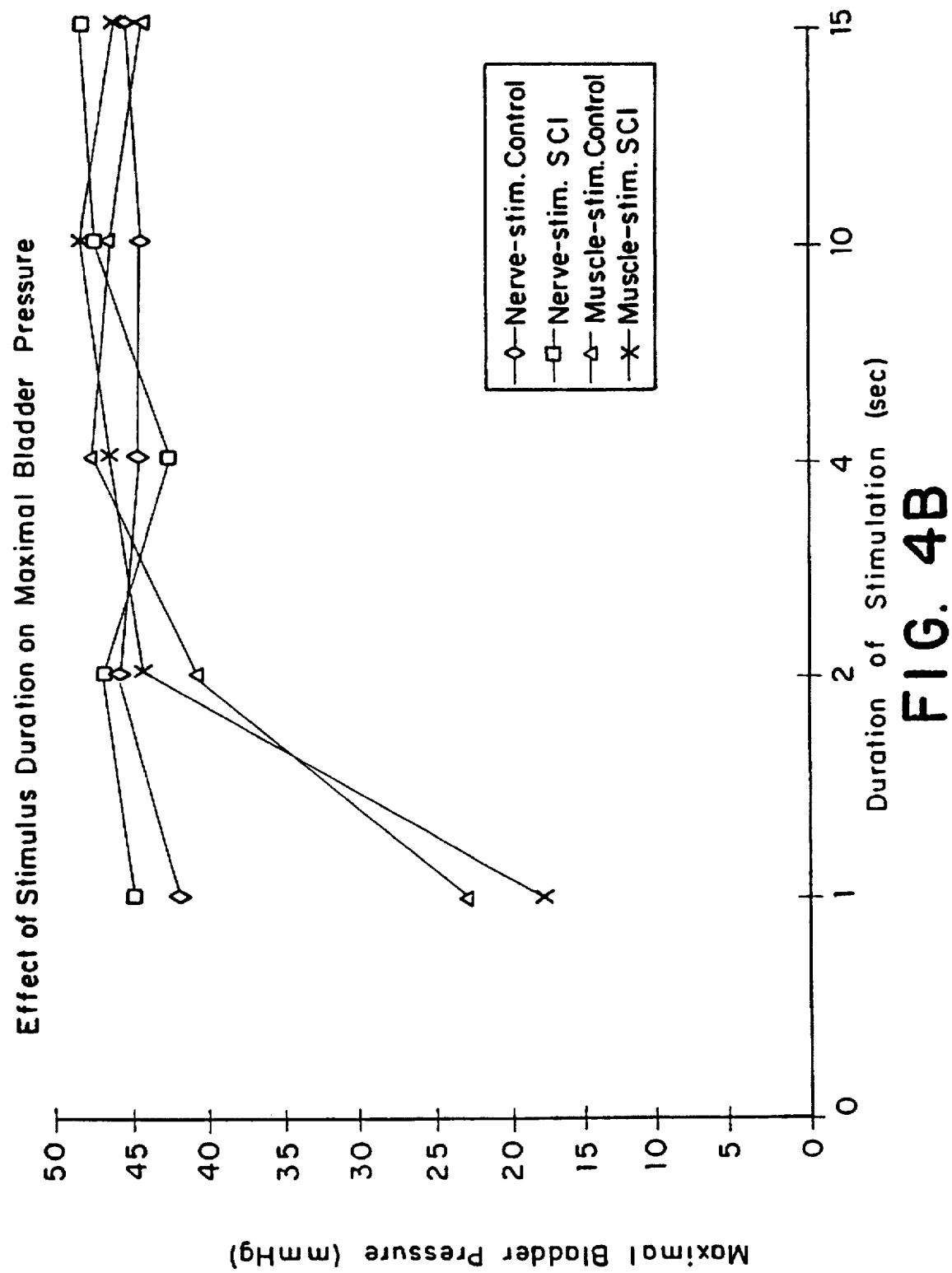

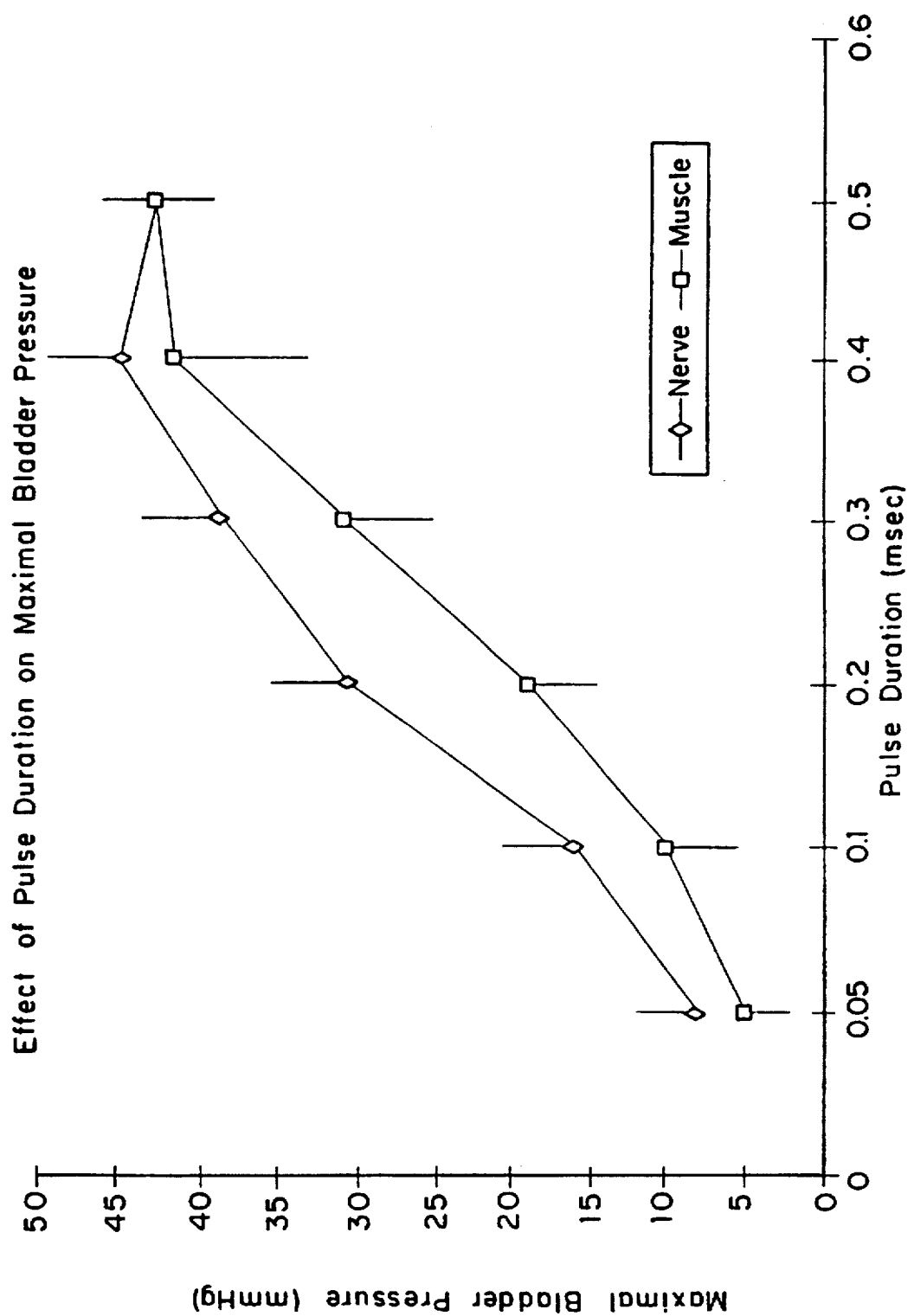

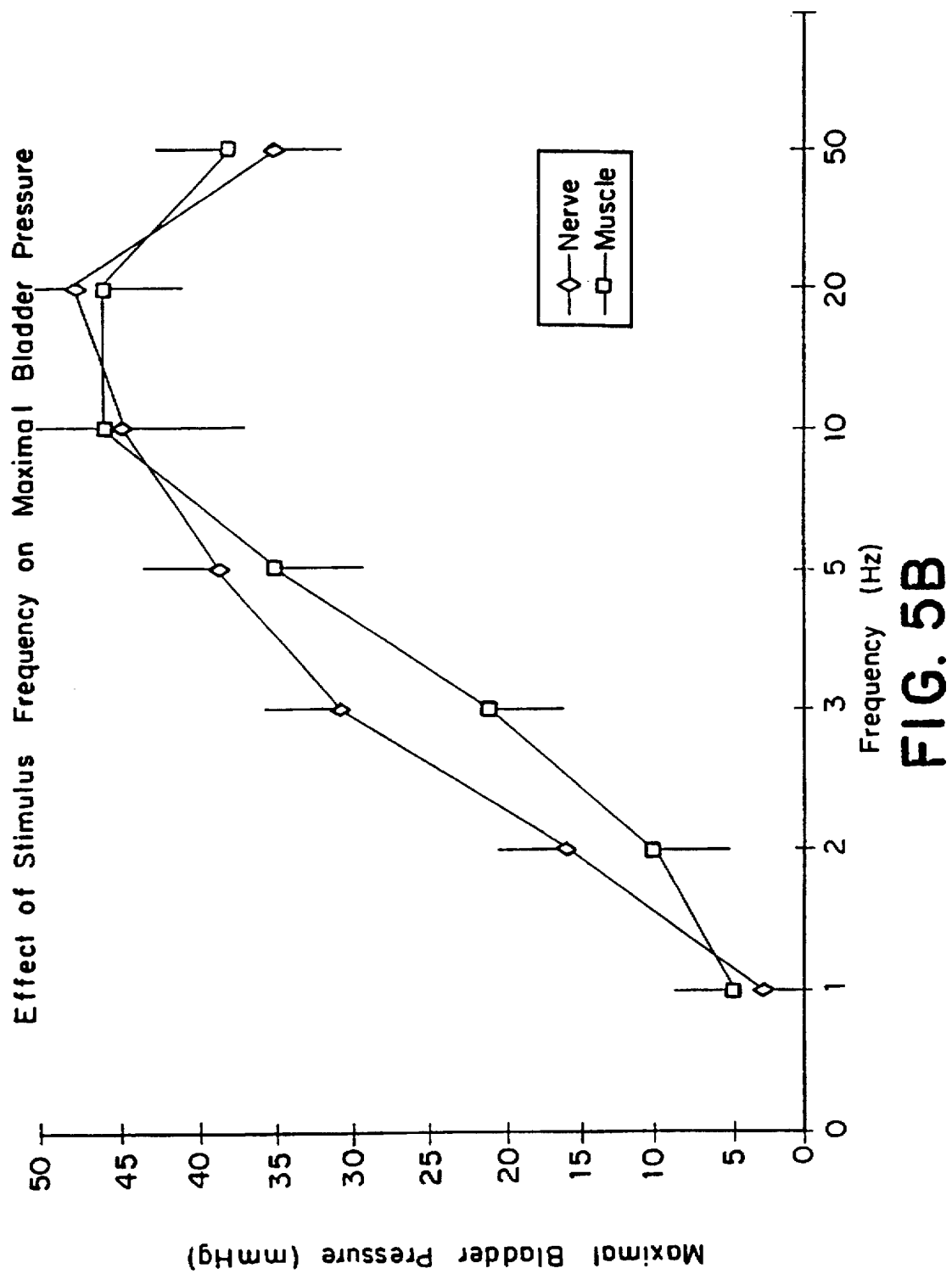

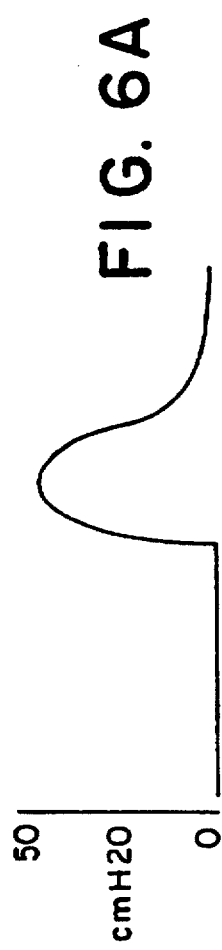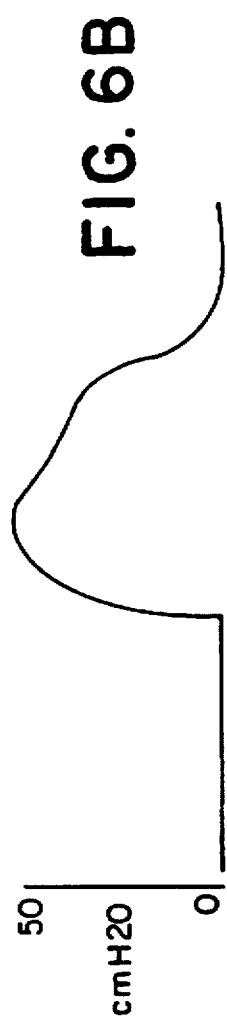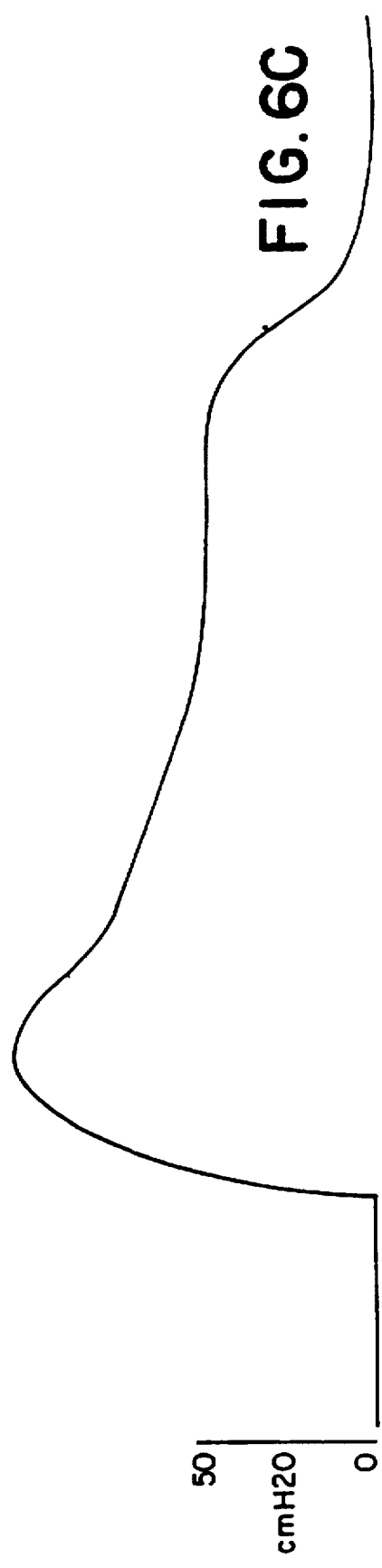

DETRUSOR MYOPLASTY AND NEURO-MUSCULAR ELECTRICAL STIMULATION

CROSS REFERENCE TO RELATED APPLICATIONS

This application is the National Stage application of PCT Application Number PCT/US94/13959 filed Dec. 6, 1994, which is a continuation-in-part application of Ser. No. 08/166,211, filed Dec. 13, 1993, which issued Dec. 6, 1994 as U.S. Pat. No. 5,370,670.

FIELD OF THE INVENTION

The present invention relates to a method of inducing micturition in individuals who are otherwise with a diminished ability or without the ability to do so. This application is U.S. Pat. No. 5,370,670, which is incorporated herein by reference.

BACKGROUND OF THE INVENTION

Functional neuromuscular electrical stimulation (FNS) to restore control over deficient muscular functions has been used as a clinical treatment of motor deficiencies for the last 20 years (Hambrecht, F. T., Reswick, J. B., (eds): Functional Electrical Stimulation: Application in Neural Prostheses. New York N.Y., Marcel Dekker, 1977). Applications include respiratory assistance by stimulation of the diaphragm in quadriplegic patients, and neuroprosthesis of the arms and legs (Hambrecht, F. T., Reswick, J. B., (eds): Functional Electrical Stimulation: Application in Neural Prostheses. New York N.Y., Marcel Dekker, 1977; Mortimer, J. T.: Motor prostheses, in Brooks (ed): Handbook of Physiology, the Nervous System. Motor Control, Bethsda, Md., 1984 Am Physiol. Soc. 2:155–187; Salmons, S. and Vrbova, G. 1969 J. Physiol. 201:535). Some of these studies have indicated that changes in muscle function occur based on the stimulation. It is known that muscle fiber composition and resulting physiologic and metabolic characteristics (force, contraction and relaxation times) depend on neural activity (Salmons, S. and Vrbova, G. 1969 J. Physiol. 201:535). By electrically controlling nerve and muscle activation, improved fatigue-resistance of atrophic, paralyzed muscles in quadriplegic patients has been reported (Peckham, H. et al. 1976 Clin. Orthop. 114:326.)

In most FNS applications, electrical stimulation is applied to muscles in situ to restore or supplement function. Recently, researchers have evaluated the use of FNS to control the function of heterotopically transferred skeletal muscles. In some cases, the muscle may perform or work very differently from its original function. Dynamic cardiomyoplasty is a procedure in which a skeletal muscle graft is applied to the myocardium and trained to contract in synchrony with the heart muscle (Chachques, J. C., et al. 1988 Circulation 78:203 (Suppl 3); Acker, M. A., et al. 1987 Science 236:324; Magovern, G. J., et al. 1988 Ann Thorac. Surg. 45:614). The first clinical cardiomyoplasty was performed in 1985 (Carpentier, A. and Chacques, J. C.: 1985 Lancet 1:1267). In the approach followed by those investigators, the latissimus dorsi muscle was conditioned to behave like a cardiac muscle by slowly increasing muscle work to adapt to a new cardiac-like function. It is estimated that over 100 cardiomyoplasties have been performed world-wide and may represent an important role in the treatment of congestive heart failure.

In the 1960's the concept of the application of functional electrical stimulation in urology began to emerge. Direct bladder surface stimulation was attempted in order to induce micturition by a patient. However, many clinicians became disenchanted because the high current required would spread to the pelvic floor mixture, causing pain and contraction of the external sphincter during micturition. Device failure was common and a fibrocapsule often developed around the bladder electrodes (Alexander, S. and Rowan, D., 1968 Br. J. Surg., 55:358; Boyce, W. H., et al. 1964 J. Urol., 91:41; Merrill, D. C. 1974 J. Urol. 112:823; Merrill, D. C. and Conway, C. J. 1974 J. Urol. 112:52; and, Timm, G. W. and Bradley, W. E. 1969 Invest. Urol. 6:562).

Throughout the 1970 and 1980's, research toward bladder stimulation was directed toward sacral anterior root stimulation in conjunction with selective or complete sacral deafferentation (Brindley, G. S. et al. 1986 J. Neurol. Neurosurg. & Psychiatry 49:1104; and, Tanagho, E. A. et al. 1989 J. Urol. 142:340). Sacral anterior root stimulation requires intact sacral motor roots and a detrusor capable of contraction.

The use of the rectus muscle to assist manual-compression bladder emptying has been reported (Zhang, Yu-Hai et al., 1990 J. Urol. 144:1194). A rectus muscle sling to suspend the bladder to a level immediately beneath the anterior rectus sheath was used, thereby allowing neurologically injured patients to empty their bladder with manual compression. The skeletal muscle flap has also been described for bladder augmentation. Direct anastomosis between skeletal muscle and the bladder wall will develop ingrowth and resurfacing of the muscle with transitional cells. Calculi and cartilaginous formation commonly occur however, complicating this technique (Buyukunal, S. N. C., et al. 1989 J. Ped. Surg. 24:586).

There is a need for an improved method of inducing micturition by an individual with an areflexic bladder. There is a need for methods of electrical muscle stimulation to induce micturition by an individual with an areflexic bladder.

SUMMARY OF THE INVENTION

It is an object of the invention to provide a system and method for inducing micturition in patients with areflexic bladders or an otherwise diminished capacity to intentionally micturate.

The present invention provides an implantable micturition inducer. The device that is the invention comprises an implantable actuatable signal generator that comprises one or more switches and a power source, and at least one electrical lead having one end connected to the signal generator and the other end adapted to be connected to muscle transected to form a muscle bag around an individual's bladder. Actuation of the switch or switches results in the delivery of a series of stimulus pulses from the signal generator to the muscle bag which are sufficient to cause the muscle bag to contract and thereby induce micturition on demand.

The present invention provides a method wherein the a muscle for a patient is transected and used to form a muscle bags around the patient's bladder or a reconstructed, augmented or created bladder. The muscle bag is attached to at least one electrical lead which is attached to an implantable actuatable signal generator that comprises one or more switches and a power source. The switch or switches of the signal generator are actuated and a series of stimulus pulses are delivered from the signal generator to the muscle bag which are sufficient to cause the muscle bag to contract.

BRIEF DESCRIPTION OF THE FIGURES

FIG. 1A is a diagram showing the human rectus abdominis muscle including innervation and vascularization, the points of attachment of the rectus abdominis muscle, and the bladder before detrusor myoplasty.

FIG. 1B is a diagram showing the human rectus abdominis muscle including innervation and vascularization, the points of attachment of the rectus abdominis muscle, and the bladder wrapped with the rectus muscle flap after detrusor myoplasty.

FIG. 2C contains data showing twenty-four hour micturition patterns of a spinal cord injured rat after detrusor-myoplasty.

FIG. 4B contains data showing the effect of stimulus duration on bladder pressure. Stimulation parameters: 0.5 msec duration at 200 V and 20 Hz with stimulus durations between 1–15 sec. Four groups of rats were studied: Nerve-stimulation of control rats, nerve-stimulation of spinal cord injured (SCI) rats, muscle-stimulation of control rats, and muscle-stimulation of SCI rats.

FIG. 5A contains data showing the effect of pulse duration on maximal bladder pressure after nerve and muscle stimulation in spinal cord injured rats. Stimulation parameters: 200 volts, 20 Hz for 2 seconds at pulse duration from 0.05 to 0.5 msec.

FIG. 5B contains data showing the effect of stimulus frequency on maximal bladder pressure after nerve and muscle stimulation in spinal cord injured rats. Stimulation parameters: 0.5 msec, 200 V for 2 seconds at frequency from 1 to 50 Hz.

FIG. 6A contains data showing bladder pressure response to detrusor-myoplasty neurostimulation in a spinal cord injured rat. Nerve stimulation: 50 V, 0.05 msec, and 50 for 2 seconds.

FIG. 6B contains data showing bladder pressure response to detrusor-myoplasty neurostimulation in a spinal cord injured rat. Nerve stimulation: 25 V, 0.05 msec, and 50 Hz for 4 seconds.

FIG. 6C contains data showing bladder pressure response to detrusor-myoplasty neurostimulation in a spinal cord injured rat. Muscle stimulation: 50 V, 0.05 msec, 50 Hz for 14.6 seconds.

DETAILED DESCRIPTION OF THE INVENTION

Figure 2A:
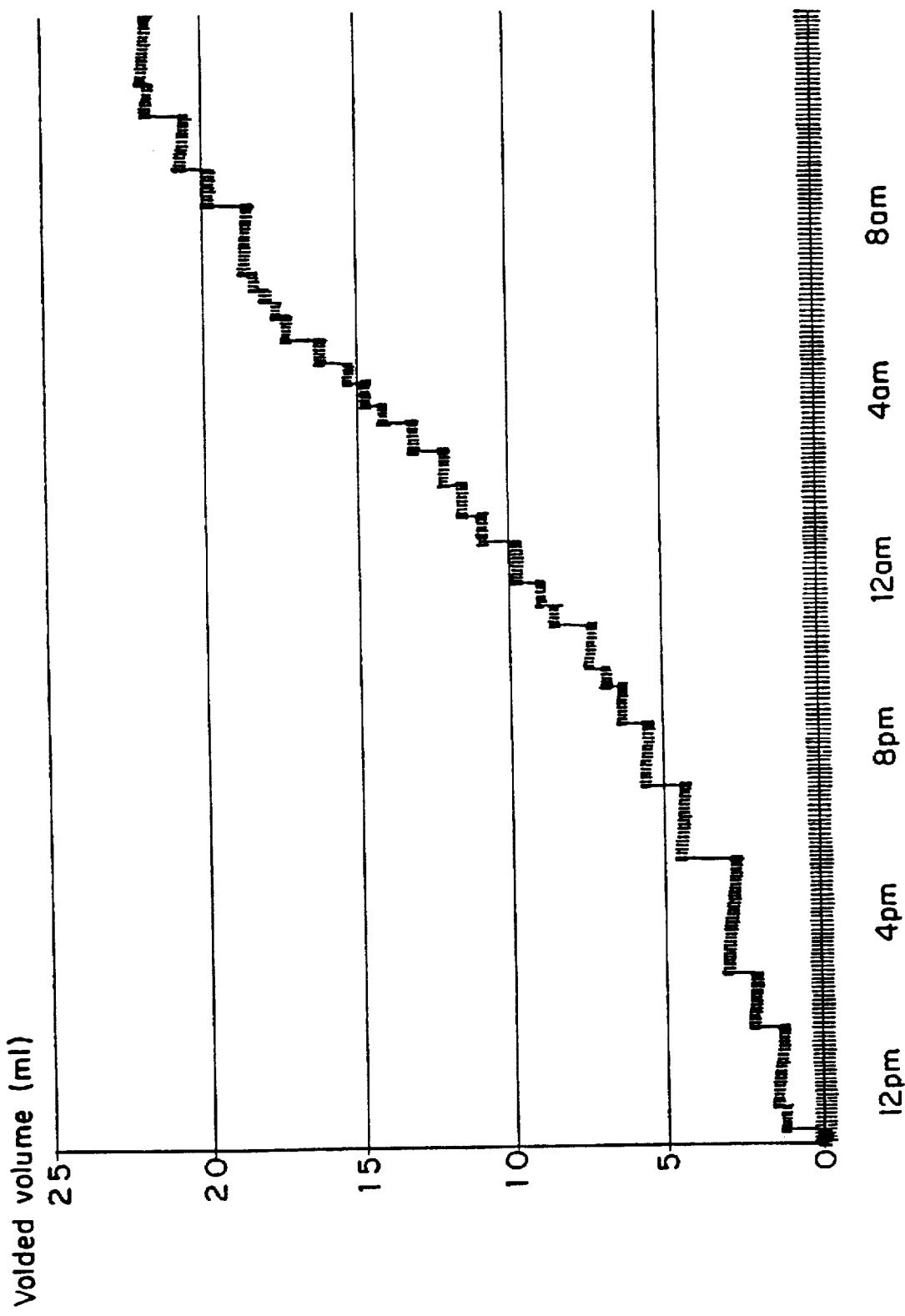
FIG. 2A contains data showing twenty-four hour micturition patterns of a control rat.

The present invention relates to devices and methods of inducing micturition in individuals with areflexic bladders. According to the present invention, a neurovascular muscle flap is surgically wrapped around the bladder. The muscle is attached to an implantable actuatable battery powered signal generator such that activating the signal generator neurostimulates the muscle which thereby contracts and induces micturition.

According to the preferred embodiments of the present invention, the rectus abdominis muscle serves as a neurovascular muscle flap for detrusor-myoplasty wherein the muscle is used to wrap around the bladder. In other embodiments, the internal oblique is used to create the muscle flap. In other contemplated embodiments, the latimus dorsi is used as a muscle tissue source which is transected, revascularized, renervated and attached with electric leads to the implantable actuatable signal generator.

In some embodiments, the bladder is reconstructed or augmented by or created from other tissue such as intestinal tissue. Bladders may be reconstructed in cases where the individual is suffering from bladder cancer and malignant tissue has been resected. In such cases, the reconstructed bladder may be augmented or enlarged by addition of intestinal tissue. In some embodiments, the individual's bladder is completely removed and a new bladder is created from intestinal tissue, particularly small intestine or colon. The reconstructed or newly created bladder is wrapped with a muscle flap and connected to an implanted actuatable signal generator by electric leads which are specifically adapted to connect the muscle to the implantable actuatable signal generator.

There are a large number of patients with areflexic bladders who may be candidates for detrusor-myoplasty. These patients are excluded from anterior root neurostimulation because they do not have an intact sacral motor root and/or their bladders cannot contract. Detrusor-myoplasty may be applicable for patients with non-intact sacral motor roots who are not candidates for sacral nerve root stimulation. Detrusor-myoplasty with neurostimulation can provide an alternative therapy for upper motor neuron neurogenic bladder dysfunction.

Detrusor-myoplasty is based on the principles of cardiomyoplasty. Muscle is transected in order to provide a contractile source to effect organ functioning. In the case of detrusor-myoplasty, muscle is wrapped around the bladder to substitute for non-functioning muscle. A source of electrostimulation is provided to initiate contraction and induce micturition. There are several potential advantages to detrusor-myoplasty over cardiomyoplasty: 1) muscle fatigue is less of a problem because muscle contraction for bladder emptying only need to occur 10 times or less per 24 hours versus 60 contractions per min for the heart; and 2) acute mechanical or electronic failure can be treated with intermittent catheterization, failure of cardiomyoplasty could immediately jeopardize the life of the patient.

The rectus abdominis muscle was found to be best suited as a neurovascular muscle flap for detrusor-myoplasty. The rectus muscle was examined in detail in the rat, goat, and human cadaver. FIG. 1A is a diagram showing the human rectus abdominis muscle including innervation and vascularization, the points of attachment of the rectus abdominis muscle, and the bladder before detrusor myoplasty.

FIG. 1A represents a preferred embodiment of the invention. As shown in FIG. 1A, the rectus abdominis muscle 1 arises from the pubic symphysis and the pubic crest, collectively shown as 7 and inserts on the fifth, sixth, and seventh costal cartilages above the costal margin, collectively shown as 8. The muscle 1 is a long and flat muscle that is transected by three tendinous intersections. It is partially ensheathed by the anterior and posterior rectus sheaths, and extends the length of the anterior abdominal wall. The rectus abdominis 1 has two major arterial pedicles. The upper pedicle is a continuation of the internal thoracic artery 3 and the lower pedicle is a branch of the external iliac artery 6.

These two arterial supplies anastomose in the mid-belly of the rectus muscle 1. There are numerous musculocutaneous perforating vessels throughout the muscle. The axial vascularization is predominant however, with the deep inferior epigastric artery 5 more significant than the superior epigastric artery 4. The inferior epigastric artery 5 is anatomically larger and physiologically "dominant" over the superior epigastric artery 4 with respect to blood supply to the muscle 1. The muscle 1 receives segmental innervation from the branches of the lower six intercostal nerves 9–14. Motor branches from the seventh through twelfth intercostal nerves 9–14 reach the muscle 1 at its deep surface. These nerves 9–14, together with the intercostal arteries, pass between the versus abdominis and the internal oblique muscles. They give several branches to the external and internal oblique muscles, then end in two perforating branches. One is a lateral cutaneous branch, the other a medial somatomotor branch that penetrates the rectus muscle 1. Long-term follow-up of patients after rectus abdominis muscle transfer for breast reconstruction has demonstrated no significant functional deficits. The sacrifice of this muscle does not negatively impact the patients' ability to move.

Detrusor myoplasty is performed as follows. As shown in FIG. 1B, the muscle 1 is transected free from the rectus fascia. The blood supply from the superior epigastric artery 4 is sacrificed and the muscle is transected midway between the xiphoid and umbilicus. The inferior epigastric artery 5 is carefully preserved. The muscle flap attached to the symphysis pubis 7 is located and used to wrap/cover the bladder 2 without tension, preserving at least two 13–14, preferably two 13–14 to four 11–14, intercostal nerves with its blood supply. Approximately ½ to ⅔ of the entire unilateral rectus muscle 1 is needed to effectively wrap the bladder 2. The muscle 1 is wrapped around the distended bladder 2 and attached to itself with sutures 18, creating a muscle "jacket" or "bag" with its content being the bladder 2. An actuatable signal generator, also referred to herein as an electrostimulator or an electrostimulation system, which includes a signal generator 15, one or more sets of leads 16 and a switch 17 is provided. Electrostimulators are similar to those commercially available and used in cardiomyoplasty and may be assembled from readily available components. Signal generators and leads such as those sold by Medtronic (Minnesota) may be modified for use in detrusor myoplasty. Generally, the electrostimulators used in detrusor-myoplasty are more simple in design and function than those used in cardiomyoplasty which must function continually synchronous with the heart. The electrostimulator is implanted in the patient and at least one set of leads 16 is connected from the signal generator 15 to one or more of the motor nerves attached to the muscle bag (two to four intercostal nerves being attached to the muscle bag: 13, 14; 12, 13, 14; or 11, 12, 13, 14) and/or muscle flap 1 for delivery of a pulse thereto.

Signal generators 15 useful in the present invention include signal generators that can deliver a series of pulses at a frequency in the range of 1 to 50 Hz, 0.01 to 1.0 msec pulse duration, 1 to 300 volts amplitude and a stimulation duration of up to 3 minutes. It is preferred that signal generator 15 is battery powered and implantable. The signal generator 15 may be of any standard design to provide such pulses; the shape of the pulses is not critical to the invention as claimed.

Examples of switches 17 useful in the method include standard electrical switches, radiofrequency controlled electromagnetic switches and magnet actuated switches. It is preferred that the switch is an implantable radiofrequency controlled electromagnetic switch. In some embodiments, two switches are provided to reduce the probability of accidental actuation of the signal generator 15. In some embodiments, the switch is an implantable radiofrequency controlled electromagnetic switch in which two frequencies are used to actuate the switch in order to reduce the probability of accidental actuation of the signal generator 15. Although the switch 17 is illustrated as a separate component, it can be designed to be integral with the signal generator unit so long as it performs the function of controlling delivery of pulses from the signal generator 15.

Examples of leads 16 useful in the method include spiral nerve electrodes or wire extramuscular leads.

The signal generator 15 and switch 17 may be external or internal, preferably internal. Preferably, the internalized device is placed in the subcutaneous tissue in the lower abdominal area.

Electrical stimulation is preferably applied to two motor nerves or directly to the muscle flap 1. Skeletal muscle contractions are controlled in magnitude and duration by the parameters of electrical stimulation. A single pulse results in a short evoked twitch contraction and a brief rise in intravesical pressure. Pulse width and amplitude modulation enables gradation of response by varying the number of activated motor units (spatial and temporal recruitment). Maximal bladder pressure increased as the frequency, pulse duration, voltage, or stimulation period were increased. Stimulation parameters range from a frequency of 1 to 50 Hz, 0.01 to 1.0 msec pulse duration, 1 to 300 volts amplitude and a stimulation duration of up to 3 minutes. Frequencies from 10 to 35 Hz, preferably 10–30 Hz, and voltages from 1 to 50 volts induce maximum bladder contraction and voiding. A pulse duration of 0.05 to 0.5 is preferred. A pulse duration of 0.3 to 0.5 msec is optimal. A stimulation duration of 0.2 to 1 minute is preferred. The ability of muscle to produce long-lasting work, as demonstrated by sustained increases in intravesical pressure, depends on stimulus amplitude, duration, and frequency.

EXAMPLES

Example 1

Detrusor-myoplasty (skeletal muscle assisted micturition) was investigated in a rat model of spinal cord injury (SCI). Detrusor-myoplasty was done in control and SCI rats and studied after one month. The rectus muscle on one side of the abdomen was dissected free from the ventral fascia and transected cephalad, above the level of the umbilicus. The muscular insertion to the symphysis pubis was left intact. Vascular flow via the inferior epigastric artery and vein was preserved. Innervation by 2 to 3 intercostal motor nerves was left intact. Postoperatively, no bowel or abdominal wall functional deficit was apparent. The rotated muscular flap remained innervated and vascularized. No difference in 24 hr micturition patterns became evident between control rats and rats with a rectus muscle-wrapped bladder when not stimulated. Stimulation of the rectus muscle-wrapped bladder (both nerve and direct muscle stimulation) was capable of generating bladder pressure (range 10 to 55 mmHg) and achieved bladder emptying. Stimulation parameters ranged from 0.05–0.5 msec duration, 1–50 Hz, and 12.5–300 volts. Less voltage was required for nerve than muscle stimulation to achieve similar intravesical pressure. In both acute experiments and in rats surviving 1 month after spinal cord injury, sustained bladder contractions continued.

Materials and Methods

Rats:

Male Sprague-Dawley rats (Charles River Laboratories, Wilmington, Mass.), weighing 250–300 gm were used. Four groups of rats were studied: 1) sham spinal cord injury (SCI) (n=8); 2) sham SCI with detrusor-myoplasty (n=5); 3) SCI rats (n=8); and 4) SCI rats with detrusor-myoplasty (n=5). The research protocol and animal usage in these studies have been approved by our Institutional Animal Care and Use Committee, and adhere to guidelines set forth by the US Department of Health, Education and Welfare's "Guide for the Care and Use of Laboratory Animals".

Anesthesia:

Anesthesia was induced in all animals using pentobarbital (65 mg/kg, intraperitoneally), with pure oxygen delivered intraoperatively through a tight-fitting mask. In all animals, rectal temperature was maintained between 37° C. and 38° C. with a heating pad.

Spinal Cord Injury:

After a sufficient depth of anesthesia was verified, the animal was positioned in a spinal stereotaxic apparatus (David Kopf, Tujunga, Calif.), with fixation at the ears. The skull was exposed, and stainless-steel jewelers' screws (Small Parts, Miami, Fla.) implanted for recording the somatosensory-evoked potential (SEP). Screws were threaded as electrodes into the skull near the union of the midline with bregma (positive) and lambda (negative) and in the nasal sinus. Stimuli were delivered through a pair of platinum subdermal needle electrodes (Grass, Quincy, Mass.) inserted in the hindlimb near the medial malleolus and plantaris tendon. Constant voltage pulses were delivered at 3 Hz at an intensity sufficient to elicit a slight twitch in the outer digits (10 to 15 V). SEPs were averaged over a 90-millisecond epoch using 256 trials and a bandpass between 3.2 and 3.2000 Hz. The latency and amplitude of the major negative wave were then measured over three to five trials prior to laminectomy.

The thoracic region of the spine was then exposed, and laminectomy performed at the T-10 level. The dura mater was left intact. The SEP was then re-evaluated in order to confirm the presence of normal conduction after laminectomy. Animals were excluded from study if the SEP latency increased by more than 2 milliseconds or if the amplitude decreased by more than 50%. Animals were prepared for injury by applying additional fixation at the T-12 spinous process using a vertebral clamp.

The injury device consisted of a hollow steel tube with a nylon impounder at the bottom (0.3 cm diameter at the tip). The impounder was free to move up into the tube but was restricted in its downward movement. After being secured to a micromanipulator, the device, with impounder tip fully extended, was lowered onto the exposed dura until contact with the cord caused the impounder to move precisely 0.2 cm up into the tube. At this point a 10 gm weight was dropped from a height of 5 cm to provide a 50 gm cm injury. Sham-injured rats underwent the impounder placement but without weight-drop. The SEP was then recorded 2, 5, 10, and 15 minutes later in order to verify the injured condition. Animals (groups 3 and 4) subjected to spinal cord injury were excluded if the SEP response was not obliterated during the entire 15 minute period following weight-drop. Similarly sham-injured animals (groups 1 and 2) were excluded if the SEP latency increased by 2 msec or amplitude decreased by $\geq 50\%$.

Neurological Evaluation:

A modified Tarlov scale (Tarlov, I. 1954 Arch. Neurol. Psychiatry 71:588) was employed weekly for 4 weeks. Each hindlimb was rated as follows:

0—total paraplegia of hindlimbs;

1B—no spontaneous movement but responds to hindlimb pinch;

2—spontaneous movement but unable to stand;

3—able to support weight but cannot walk on broad, flat surface;

4—able to walk on broad, flat surface;

5—able to walk on broad, flat surface and support weight on a 1.8-cm-wide ledge; and 6—able to walk on ledge.

The final scores are reported. The Rivlin-Tator angleboard test (Rivlin, A. S. and Tator, C. H. 1977 J. Neurosurg. 47:577) was also performed weekly and before the animals were sacrificed. The maximum angle maintained for 5 seconds or longer was measured, and averaged to yield a final value.

Micturition Patterns:

The rats were placed in a metabolic cage that could deflect the voided urine. The deflected urine was collected for 24 hour periods on an electronic scale (Scientech ESL/1000; Boulder, Colo.) and constantly monitored by a microcomputer for the recording of micturition frequency, duration, and volume. Data were recorded and stored using Lotus Measure data acquisition software (National Instruments, Austin, Tex.).

Parameters analyzed were: 1) total urine volume/24 h; 2) number of micturitions/24 h; 3) mean volume of each void; 4) oral fluid intake/24 h; 5) ratio of micturitions-night vs. day; 6) largest micturitional volume; and 7) smallest micturitional volume.

Detrusor-Myoplasty Technique:

Unilateral dissection under magnification was directed to the rectus abdominis muscle using a midline incision. The entire width of the muscle was elevated creating a muscle flap averaging six centimeters in length. The muscle was transected cephalad, above the level of the umbilicus. The attachment to the pubic symphysis and the inferior epigastric artery were carefully preserved. Laterally, 2 to 3 intercostal motor nerves were elevated to the rib tips and preserved with the muscle flap. The bladder was then exteriorized, cannulated at the level of the urethra using a modified 18 Gauge spinal needle, and connected to a Statham P-23 pressure transducer. At this point the muscle was wrapped around the distended bladder and sutured (3-0 Vicryl$^R$) to itself, creating a muscle bag, with its content being the bladder. In another 3 SCI rats that underwent detrusor-myoplasty, a 20 gauge intravenous infusion catheter was sutured to the dome of the bladder. Micturition could thereby be directly observed at the urethral meatus after electrostimulation.

Electrical Stimulation:

Stimulation parameters ranged from a frequency of 1 to 50 Hz, 0.05 to 0.5 msec pulse duration, and 12.5 to 300 volts amplitude. Electrical stimulation was applied to two motor nerves or directly to the muscle flap.

Blood Flow Measurement:

Blood flow within the muscle was monitored by laser Doppler flowmetry (BMP 403A, LaserFlow Inc., St. Paul, Minn.). The probe was placed on the surface of the muscle belly to continuously monitor blood flow in 1 mm$^3$ of the underlying cape beds during stimulation.

Data Analyst:

Parametric measures were compared via analysis of variance (ANOVA) followed by Tukey's post-hoc analysis. Ordinal neurologic outcome scores were compared by the Kruskal-Wallis ANOVA followed by the Mann Whitney U-test. A p value less than 0.05 for both the ANOVA and post-hoc test was considered significant.

Results

The median final neurological outcome as measured by the modified Tarlov ratings for all animals who survived 30 days after spinal cord injury was 5, reflecting the presence of spontaneous movement both hindlimbs, weight-bearing ability in one hindlimb, but the absence of locomotor function. Sham operated SCI rats that did and did not undergo detrusor-myoplasty all had normal final Tarlov scores of 12. Creation of detrusor-myoplasty did not alter Tarlov ambulation scores or the inclined angle scores (Table 1).

Figure 2B:
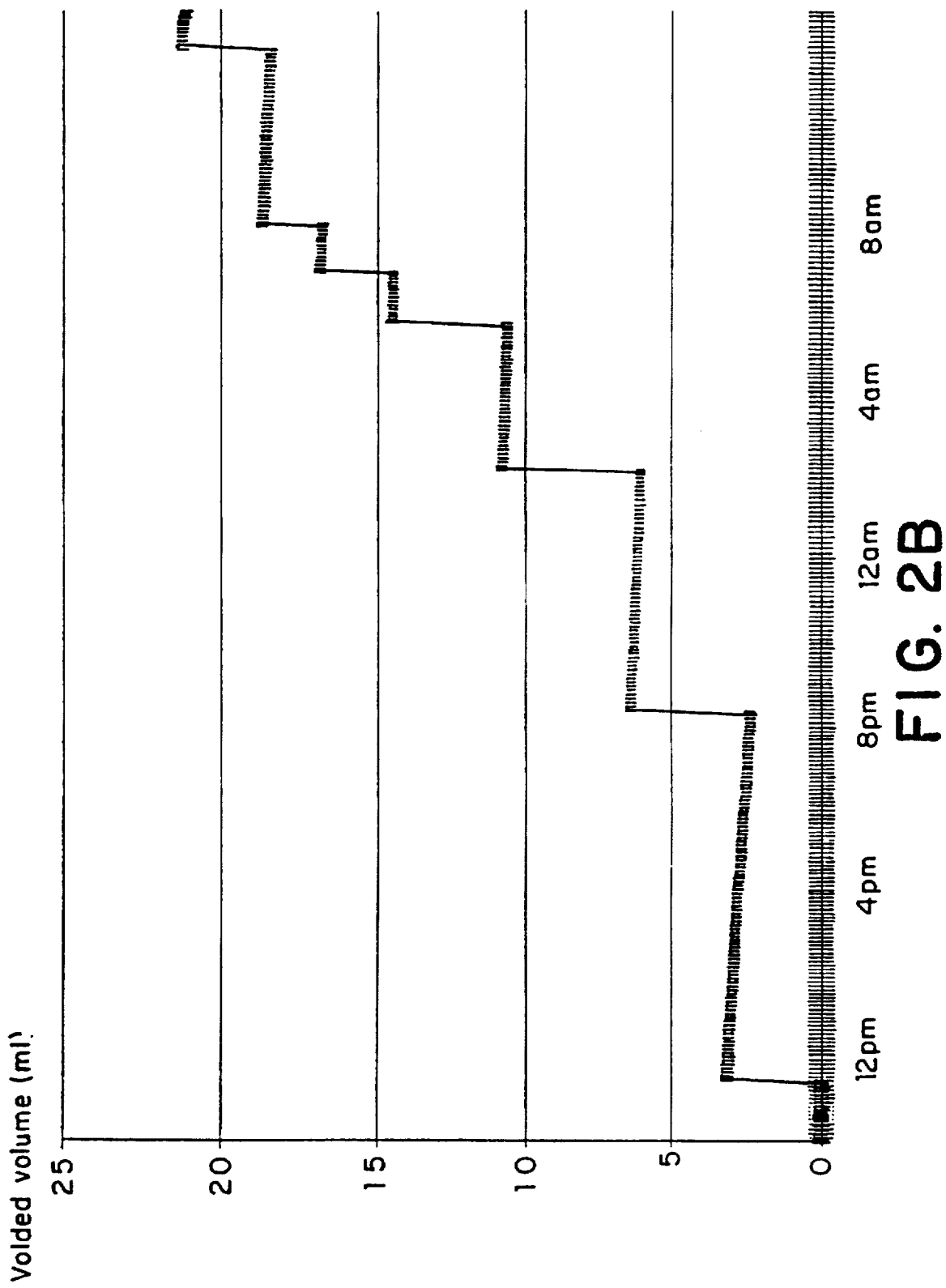
FIG. 2B contains data showing twenty-four hour micturition patterns of a spinal cord injured rat.

Analysis of 24 hr micturition patterns demonstrated no differences in oral fluid intake/24 hr, voided volume/24 hr, and ratio of number of micturitions during the night vs day among the four groups. Spinal cord injured rats with and without detrusor-myoplasty had a significant decrease in the number of micturitions/24 hr, an increase in volume per micturition, and greater largest and smallest micturition volumes (Table 2, FIG. 2A, FIG. 2B and FIG. 2C). The micturition patterns were similar among rats in both the sham and SCI groups with and without detrusor-myoplasty. The performance of detrusor-myoplasty without electrical stimulation did not enhance or interfere with the functional status of the rat based on Tarlov locomotor score, angleboard score, and micturition patterns.

No complications from the procedure of muscle-wrapping developed; neither hernia nor bowel obstruction were seen. Two rats died within 5 days after the initial spinal cord injury, and both manifested urinary tract sepsis.

Laser Doppler flowmetry displayed similar blood flow values in the rectus muscle flap immediately after superior epigastric division, and 1 month after muscle transposition. Muscle blood flow values for the flap and the contralateral undissected rectus muscles were not significantly different at 97±34 and 105±40 (ml/100 g tissue min.), respectively ($p=0.47$). Similar blood flow values were seen before, during, and after electrical stimulation.

Figure 3:
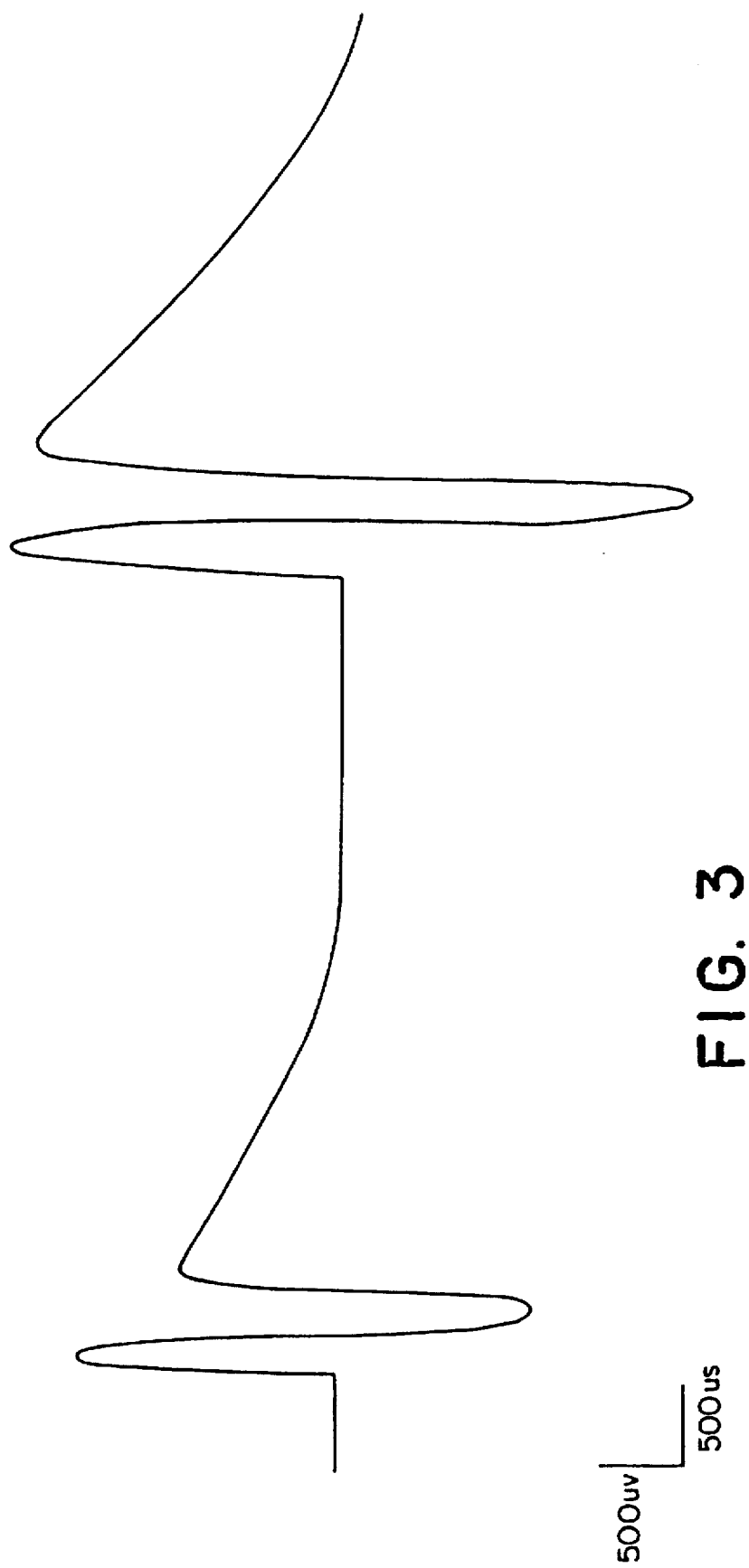
FIG. 3 shows an electromyographic recording of rectus muscle electrical potentials with nerve stimulation in a rat 4 weeks after spinal cord injury and detrusor-myoplasty. Single stimulation parameters: A) 50 V, 0.5 msec, and B) 100 V, 0.5 msec. Note the M wave potentials indicating viable innervation of the muscle flap.
Figure 4A:
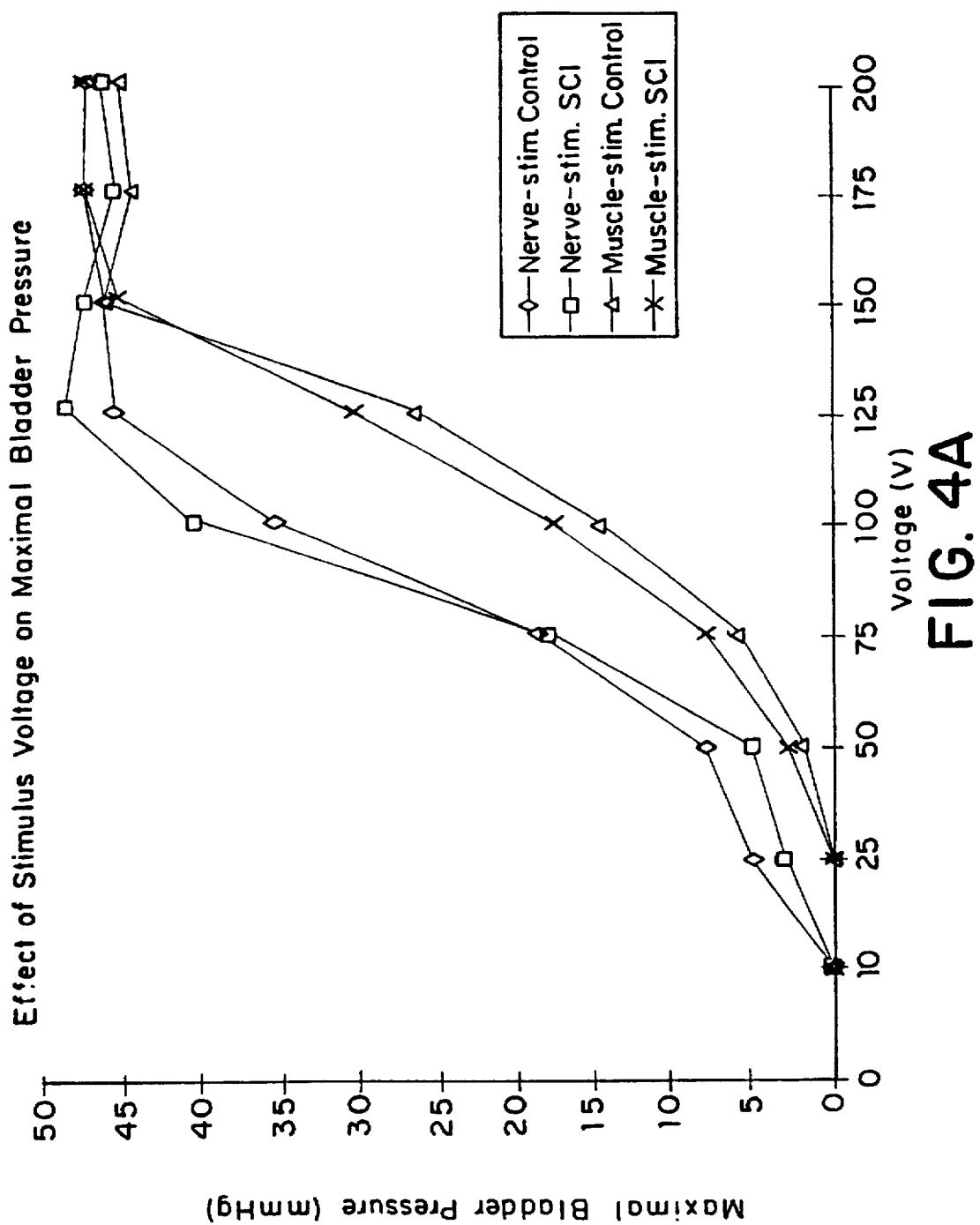
FIG. 4A contains data showing the effect of stimulus voltage on bladder pressure. Stimulation parameters: 0.5 msec duration at 20 Hz for 2 seconds at voltage between 10–200 V. Nerve-stimulation of control rats, nerve-stimulation of spinal cord injured (SCI) rats, muscle-stimulation of control rats, and muscle-stimulation of SCI rats.

Skeletal muscle contractions could be controlled in magnitude and duration by the parameters of electrical stimulation. A single pulse resulted in a short evoked twitch contraction and a brief rise in intravesical pressure (FIG. 3). Pulse width and amplitude modulation enabled gradation of response by varying the number of activated motor units (spatial and temporal recruitment). Maximal bladder pressure increased as the frequency, pulse duration, voltage, or stimulation period were increased. Frequencies from 10 to 35 Hz and voltages from 150 to 300 volts induced maximum bladder contraction and voiding. A long pulse duration 0.3 to 0.5 msec was optimal. The ability of muscle to produce long-lasting work, as demonstrated by sustained increases in intravesical pressure, depended on stimulus amplitude, duration, and frequency (FIG. 4A, FIG. 4B, FIG. 5A and FIG. 5B).

Both nerve and direct muscle stimulation were able to generate detrusor contraction and increase intravesical pressure. The rectus muscle contraction and increase in intravesical pressure was sustained for the duration of electrical stimulation (FIG. 6A, FIG. 6B and FIG. 6C). The maximal detrusor pressure was similar between sham and SCI rats that had detrusor-myoplasty. Bladder emptying could be achieved with both nerve and muscle stimulation. Less stimulation voltage was required for nerve versus direct muscle stimulation to achieve bladder emptying.

Example 2

Detrusor-myoplasty dissection was also performed in 2 female goats. The rectus abdominis muscles were used for bladder wrapping. The goat bladder is a pelvic organ of greater than 100 ml in capacity with detrusor wall thickness similar to the human. The rectus muscle in the goat is wide but thin. The rectus muscle was dissected free from the overlying fascia while preserving 2 motor nerves. The muscle flap, attached only interiorly to the pubic symphysis, could reach and wrap around the bladder without tension. Considering the similarity in size and proportion of goat anatomy, the goat is a good chronic detrusor-myoplasty model for human study.

Example 3

Rectus abdominis muscles were used for bladder wrapping in 3 fresh human cadavers (2 female, 1 male). In all 3 human cadavers it was possible to dissect the rectus muscle in its entirety and isolate and preserve 3 motor nerves. Dissection of cadavers confirmed the segmental innervation of the rectus abdominis muscle by the terminal branches of the lower six intercostal nerves. The nerves pass with the intercostal arteries deep to the internal oblique muscle and superficial to the versus abdominis muscles. The nerves penetrate the sheath of the rectus muscle lacy to enter the muscle belly ventrally. The muscle was dissected free from the rectus fascia, leaving only the attachment to the symphysis pubis. The blood supply from the superior epigastric artery was sacrificed and the muscle was transected midway between the xiphoid and umbilicus. The inferior epigastric artery was carefully preserved. The muscle flap was located and used to wrap the bladder without tension, preserving 3 nerves with its blood supply. Approximately ½ to ⅔ of the entire unilateral rectus muscle is needed to effectively wrap the bladder. No difficulty in abdominal closure occurred.

Example 4

Transection of the rectus abdominis muscle around the bladder was performed on a patient. Neurovascular innervated rectus abdominis muscle wrap of the urinary bladder restored micturition. The patient was a 33-year old male paraplegic who suffered an $L_{4-5}$ spinal cord injury secondary to a gunshot wound to the spine in 1980 and who has been managed with a suprapubic tube since the injury. The patient complained of constant suprapubic pain, leakage of urine per urethral meatus and recurrent febrile urinary tract infections. Video-urodynamics demonstrated a poorly compliant bladder with a capacity of less than 100 ml and grade II left vesicoureteral reflux.

Surgery was done through a midline abdominal incision and the suprapubic tract was excised. Bladder augmentation was first done using 15 cm of the terminal ileum. The isolated ileum was detubularized and anastomosed to the bladder which was opened in a clam fashion. The entire width of the left rectus muscle was elevated and transected cephalically above the level of the umbilicus. The inferior pubic symphysis attachment and inferior epigastric artery were preserved. Laterally, 3 intercostal motor nerves were elevated to the rib tips and preserved with the muscle flap. At this point the muscle was wrapped around the augmented bladder and sutured (0 Vicryl[R]) to itself, creating a muscle bag, with its content being the bladder.

The postoperative course was remarkable for a bout of pseudomembranous colitis. The patient has sensation of filling and fullness. No urine leakage or bladder perforation occurred. Intermittent clean catheterization was instituted on the seventh postoperative day. No bowel or abdominal wall functional deficit was apparent. After 30 days the patient was taught to volitionally contract his rectus muscle to urinate.

Example 5

The following is a description of the detrusor-myoplasty in which an electrostimulation system is attached to a transected rectus abdominis muscle wrapped around the urinary bladder to restore micturition. Briefly, surgery is done through a midline abdominal incision and the suprapubic tract is excised. Bladder augmentation is first done using 15 cm of the terminal ileum. The isolated ileum is detubularized and anastomosed to the bladder which is opened in a clam fashion. The rectus abdominis muscle is used for detrusor-myoplasty. The entire width of the left rectus muscle is elevated and transected cephalically above the level of the umbilicus. The inferior pubic symphysis attachment and inferior epigastric artery are preserved. Laterally, 3 intercostal motor nerves are elevated to the rib tips and preserved with the muscle flap. At this point the muscle is wrapped around the augmented ladder and sutured (0 Vicryl$^R$) to itself, creating a muscle bag, with its content being the bladder. An electrostimulator which includes a power supply, leads and a switching mechanism is provided internally. The leads are attached to the rectus abdominis muscle and/or one or more of the intercostal motor nerves. The other end of the lead is attached to the power supply by way of the switch. The following is a detailed description of the procedure.

The patient is placed supine on the operating table. The patient's abdomen and genitalia are prepped and draped in the usual sterile fashion. The patient is anesthetized and intubated. A lower abdominal midline incision is made around, and the suprapubic tract is isolated by incising on both sides. Dissection is carried down to the anterior rectus fascia which is incised with Metzenbaum scissors. The anterior rectus sheath is then opened using electrocautery. The dissection is then carried down to the peritoneum which is grasped with forceps and incised. The peritoneum is then entered. The suprapubic tract is isolated and the skin surrounding the tract is grasped using Allis clamp and the entire tract is excised using sharp and blunt dissection all of the way down to the bladder which is then opened at the suprapubic tract site.

The bladder is freed from adhesions. A midline incision is made in the bladder from the posterior wall all of the way down to the bladder neck anteriorly. Hemostasis is achieved using electrocautery. A segment of small bowel approximately 1 foot proximal to the ileocecal valve is isolated. Incisions are made in the mesentery, taking care to preserve the blood supply to the segment of bowel, approximately 10 inches in length. Using clamps and 3-0 silk ties, the mesentery is incised and ligated, and the ileum is resected using GIA stapler. The ileum is then reconstituted using a stapled anastomosis. This is reinforced using 3-0 silk interrupted sutures. The anastomosis is created using TIA stapler, taking care to use it on the anti-mesenteric border.

The segment of ileum is then swung down to the bladder and its anti-mesenteric border is incised. The segment of bowel is then used to augment the bladder in such a way as the piece of ileum is then sutured to the bladder wall using 0 Vicryl sutures in running fashion. Suturing the ileum and bladder creates a water-tight seal which is confirmed by putting saline in through the Foley catheter. Any small leaks are sutured shut using interrupted 0 Vicryl.

Next, attention is turned to the left rectus abdominis muscle. The rectus fascia is incised medially and the rectus is dissected free of the posterior and anterior rectus sheaths, using sharp and blunt dissection. The superior epigastric vessels are identified and ligated. The rectus abdominis muscle is then transected several cms below the costal margin. The lateral neurovascular bundles are then identified segmentally from about the level of the T10 or T11. These nerves are traced back along the lateral abdominal wall, so as to free them up from their surrounding tissues. Gradually, the rectus abdominis muscle is brought down further and further into the pelvis. The muscle with its nerve supply intact is then wrapped around the neobladder, and sutured to itself and bladder using 0 Vicryl interrupted sutures. A nerve stimulator is used to confirm the nerve supply to the rectus abdominis muscle was still intact. Pressure was then applied to the sites which were bleeding until hemostasis was achieved.

Hemostasis is then achieved using electrocautery in the bed where the rectus abdominis is previously lain. Two JP drains are placed in the pelvis and one is placed in the space where the rectus abdominis is taken form along the left side. These are placed to bulb suction.

The midline wound is then closed using one PDS in running and interrupted sutures. Skin is then closed using staples. The patient is taken to the Recovery Room. Sponge and needle counts are performed two times to ensure accuracy.

TABLE 1

Animal Behavioral Data.

| Group/ Measure | Control | Control + Myoplasty | SCI | SCI + Myoplasty |
|---|---|---|---|---|
| Weight$^A$ | 391 ± 35 | 375 ± 50 | 400 ± 24 | 389 ± 40 |
| Final Tarlov Score$^B$ | 12 | 12 | 5* | 4* |
| Final Angleboard Score$^c$ | 80 ± 5 | 80 ± 5 | 65 ± 8** | 60 ± 6** |

SCI: Spinal cord injury.
$^A$: Weight in grams (mean ± S.E.M.) at time of surgery.
$^B$: Tarlov score (median) prior to sacrifice (4 weeks).
$^C$: Angleboard score in degrees (mean ± S.E.M.) prior to sacrifice (4 weeks).
*p < 0.05 vs. control and control + myoplasty, Mann-Whitney U-test.
**p < 0.05 vs control and control + myoplasty, Mann-Whitney U-test.

TABLE 2

Micturtion Pattern.

| | Control | Control + Myoplasty | SCI | SCI + Myoplasty |
|---|---|---|---|---|
| Oral intake/24 hr (ml) | 38 ± 5 | 41 ± 7 | 45 ± 11 | 41 ± 5 |
| Voided volume/24 hr (ml) | 16 ± 4 | 18 ± 5 | 19 ± 4 | 17 ± 5 |
| Number of micturitions | 18 ± 4 | 21 ± 5 | 9 ± 3* | 10 ± 4* |
| Volume per mict (ml) | 0.8 ± 0.2 | 0.7 ± 0.1 | 2.1 ± 0.5* | 1.9 ± 0.6* |
| Ration of night/day mict. | 1.8 ± 0.6 | 1.9 ± 0.5 | 2.0 ± 0.7 | 1.7 ± 0.4 |
| Largest mict. volume (ml) | 1.5 ± 0.4 | 1.9 ± 0.5 | 3.1 ± 0.7* | 2.6 ± 0.6* |
| Smallest mict. volume (ml) | 0.1 ± 0.1 | 0.2 ± 0.1 | 0.8 ± 0.3* | 0.6 ± 0.2* |

SCI: Spinal cord injury.
Mict: Micturition.
*p < 0.05 vs. control and control + myoplasty, ANOVA and Tukey's HSD test.

I claim:

1. A method of inducing micturition by a patient comprising the steps of:
   a) transecting an abdominal muscle of said patient to create a muscle flap attached, wherein blood supply and innervation to said muscle flap is preserved,
   b) wrapping said muscle flap around said patient's bladder and suturing said muscle flap to itself creating a muscle bag around said bladder;

c) attaching to said muscle bag or at least one preserved nerve at least one electrical lead;

d) attaching the other end of an electrical lead that is attached to said muscle bag or intercostal nerve to an actuatable signal generator that comprises one or more switches and a power source; and e) actuating said switch or switches and delivering a series of stimulus pulses from said signal generator to said muscle bag sufficient to cause said muscle bag to contract.

2. The method of claim 1 wherein said power source of said actuatable signal generator is a battery.

3. The method of claim 1 wherein two leads are attached to said actuatable signal generator and to two nerves that innervate said muscle flap.

4. The method of claim 1 wherein a lead is attached to said muscle bag.

5. The method of claim 1 wherein two leads are attached to said actuatable signal generator and to said muscle bag.

6. The method of claim 1 wherein said stimulus pulses are delivered at a frequency of 1 to 50 Hz, with each said pulse having a 0.01 to 1.0 msec pulse duration, 1 to 300 volt amplitude and a stimulation duration of up to 3 minutes.

7. The method of claim 1 wherein said stimulus pulses are delivered at a frequency of 10 to 35 Hz, with each said pulse having a pulse duration of 0.05 to 0.5 msec and said series has a duration of 0.2 to 1 minute.

8. The method of claim 1 wherein said stimulus pulses are delivered at a frequency of 10 to 30 Hz, with each said pulse having a pulse duration of 0.3 to 0.5 msec and said series has a duration of 0.2 to 1 minute.

9. The method of claim 1 wherein said stimulus pulses range from 1 to 50 volts.

10. The method of claim 1 wherein said actuatable signal generator comprises a switch that is a radiofrequency controlled electromagnetic switch or a magnetic switch.

11. The method of claim 1 wherein said actuatable signal generator comprises two switches wherein at least one is a radiofrequency controlled electromagnetic switches or magnetic switches.

12. The method of claim 1 wherein said actuatable signal generator comprises a switch that is a radiofrequency controlled electromagnetic switch.

13. The method of claim 1 wherein said actuatable signal generator comprises two switches that are both radiofrequency controlled electromagnetic switches.

14. The method of claim 1 wherein said actuatable signal generator comprises one switch that is a magnetic switch.

15. The method of claim 1 wherein at least one lead comprises a spiral nerve electrode.

16. The method of claim 1 wherein at least one lead is a wire extramuscular lead.

* * * * *

UNITED STATES PATENT AND TRADEMARK OFFICE
CERTIFICATE OF CORRECTION

PATENT NO. : 5,752,978
DATED : May 19, 1998
INVENTOR(S) : Michael B. Chancellor

It is certified that error appears in the above-identified patent and that said Letters Patent is hereby corrected as shown below:

Col. 8, line 2, change "113" to --1--.

Signed and Sealed this

Eighth Day of September, 1998

Attest:

BRUCE LEHMAN

*Attesting Officer*    *Commissioner of Patents and Trademarks*